US011160446B2

(12) United States Patent
Siccardi et al.

(10) Patent No.: US 11,160,446 B2
(45) Date of Patent: Nov. 2, 2021

(54) ARTHROSCOPE (71) Applicant: MEDACTA INTERNATIONAL SA, Castel San Pietro (CH)

(72) Inventors: Francesco Siccardi, Castel San Pietro (CH); Sascha Berberich, Castel San Pietro (CH); Ernst Kehrli, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 358 days.

(21) Appl. No.: 16/305,442

(22) PCT Filed: May 17, 2017

(86) PCT No.: PCT/IB2017/052898
§ 371 (c)(1),
(2) Date: Nov. 29, 2018

(87) PCT Pub. No.: WO2017/208102
PCT Pub. Date: Dec. 7, 2017

(65) Prior Publication Data
US 2019/0274535 A1    Sep. 12, 2019

(30) Foreign Application Priority Data
May 31, 2016    (IT) .................. 102016000056007

(51) Int. Cl.
*A61B 1/00* (2006.01)
*A61B 1/317* (2006.01)
*G02B 23/24* (2006.01)

(52) U.S. Cl.
CPC .......... *A61B 1/317* (2013.01); *A61B 1/00105* (2013.01); *A61B 1/00135* (2013.01); *G02B 23/2476* (2013.01)

(58) Field of Classification Search
CPC . G02B 23/2476; A61B 1/317; A61B 1/00105; A61B 1/00135; A61B 1/00142;
(Continued)

(56) References Cited

U.S. PATENT DOCUMENTS 4,896,986 A    1/1990 Terayama
6,761,684 B1   7/2004 Speier
(Continued)

FOREIGN PATENT DOCUMENTS

DE    202013100878 U1    6/2013
EP    2679178 A1    1/2014
(Continued)

OTHER PUBLICATIONS

Machine translation of JP2004261344 (Year: 2004).*
(Continued)

*Primary Examiner* — Timothy J Neal
(74) *Attorney, Agent, or Firm* — Meunier Carlin & Curfman LLC (57) ABSTRACT

An arthroscope comprises a sleeve having an internally hollow, proximal portion and an internally hollow middle portion connected to the proximal portion so as to create a through axial cavity. The sleeve has, within the middle portion, an abutment area. The arthroscope also comprises an optical unit having an elongated portion and a coupling portion configured to be at least partially received inside the through axial cavity of the sleeve. The coupling portion has a matching area suitable to couple with the abutment area. The matching area and the abutment area are shaped so as to have at least one pilot element so as to determine a univocal predefined coupling position between the sleeve and the optical unit; the matching area and the abutment area are also shaped so as to guide and automatically place the optical unit in such a predefined position.

8 Claims, 6 Drawing Sheets (58) Field of Classification Search
CPC .......... A61B 1/00131; A61B 1/00147; A61B 1/00154
See application file for complete search history.

(56) References Cited

U.S. PATENT DOCUMENTS 8,888,689 B2 * 11/2014 Poll .................. A61B 1/127
600/159
2008/0045859 A1 2/2008 Fritsch

FOREIGN PATENT DOCUMENTS

| | | |
|---|---|---|
| JP | S63-095030 A | 4/1988 |
| JP | S63169101 U | 11/1988 |
| JP | H01211716 A | 8/1989 |
| JP | H05228160 A | 9/1993 |
| JP | H06254096 A | 9/1994 |
| JP | 2004261344 A | 9/2004 |
| JP | 2006218240 A | 8/2006 |
| JP | 2010522626 A | 7/2010 |
| JP | 20140004370 A | 1/2014 |
| WO | 2008121794 A1 | 10/2008 |

OTHER PUBLICATIONS

International Search Report and Written Opinion from European Patent Office acting as the International Searching Authority for PCT Application No. PCT/IB2017/05289; dated Aug. 23, 2017; 8 pages.
English Translation of Notice of Reasons for Refusal issued in JP 2018-562575, dated Oct. 1, 2019.

* cited by examiner

ARTHROSCOPE

The present invention applies to the field of arthroscopic surgery and in particular refers to an arthroscope.

Said arthroscope finds useful application in minimally invasive surgical operations, especially when carried out as closed procedures.

Every year, a large number of patients turns to arthroscopic surgery in order to obtain functional recovery of an articulation damaged by diseases such as, for example, inflammation, acute or chronic injury.

During said interventions, functional recovery of the damaged articulation is effected by accessing it through small incisions made in the patient's limb. Said small incisions are variable in number and dimensions depending on the type of operation to be performed.

A typical arthroscopic operation involves the formation of two or more cuts in close proximity to the articulation to be operated, through which suitable operating instruments are inserted. One of these instruments is the arthroscope, which performs the function of allowing the surgeon to see the operative site.

The arthroscope known in the state of the art substantially consists of an elongated, cylindrical and axially hollow central body having proximal and distal ends, which are both open, referred to as sleeve; a cylindrical rod, referred to as shutter, which is suitable to be inserted in the axial cavity of the sleeve for the removal of body debris therein, and then removed, and has a sharp portion at its proximal end; an optical unit adapted, in turn, to be received inside said axial cavity of the sleeve so as to allow vision inside the operative site. The optical unit in turn comprises an elongated portion containing lighting and vision means; a matching portion adapted to juxtapose against a corresponding abutment portion present in the sleeve, and shaped complementarily thereto; an outer portion comprising the necessary links to external equipment such as light sources and video monitors.

The known arthroscope allows a liquid, for example water, to be introduced in the patient's body in order to improve the surgeon's vision. To do this, the sleeve of the arthroscope is provided with an inlet nozzle, through which the liquid flows, through the sleeve, into the area to be operated, and an outlet nozzle, through which the liquid is drained.

When in use, the arthroscope appears as a single body in which the sleeve, inserted inside the patients' body, is coupled to the optical unit. Said coupling must be as stable as possible in order to prevent vibration, misalignment, image distortion, poor illumination of the operative site, with consequent worsening of the surgeon's vision.

Unfortunately, what is known in the state of the art does not meet the requirements listed above.

In fact, in a known arthroscope, the coupling between the sleeve and the optical unit occurs by inserting the latter in the sleeve, and the relative position between the two components of the instrument is determined by the juxtaposition of the matching portion of the optical unit with respect to the abutment portion of the sleeve. In the state of the art, the matching portion of the optical unit generally has a frusto-conical shape, while the abutment portion is suitably shaped complementarily thereto. Said coupling allows axial rotation of the optical unit with respect to the sleeve in which it is inserted, with consequent rotation of the visual field of the surgeon.

It should also be noted that, since the optical unit consists of an elongated portion having a much smaller section than the axial extension, there may be misalignment of the elongated portion with respect to its theoretical central axis. Said misalignment, in case of rotation of the optical unit, can cause deviation of the pointing of said optical unit, thus preventing the surgeon from having visual access to a particular point of the operative site. In this case, the surgeon must proceed by trial and error to reposition the optical unit with respect to the sleeve, until he/she finds the right position for a perfect view.

Further, during the coupling between the sleeve and the optical unit, the surgeon should be careful to insert the optical unit with the right orientation, so as to obtain an image of the operative site, which is correctly oriented in space. In fact, the shape of the matching portion, and consequently of the abutment portion is unable to prevent relative rotation between the optical unit and the sleeve around the central axis of the two bodies, thus obliging the surgeon to search for the correct angular orientation of the optical unit with respect to the sleeve.

Finally, again due to the shape of the matching portion and of the corresponding abutment portion, micro-movements may occur between the two portions due to machining tolerances which generate vibrations in the visual field of the surgeon.

The object of the present invention is to solve the above drawbacks by providing an arthroscope whose main feature is the subject of claim 1.

By means of a proper conformation of the coupling between the sleeve and the optical unit, in fact, the present invention provides an arthroscope that can be put in place by the surgeon so as to automatically obtain the correct orientation of the visual field required for acting on the operative site.

The suitable complementary shaping of the matching portion and the abutment portion allows an univocal coupling direction which prevents relative rotations, minimises vibrations due to machining tolerances and allows the surgeon not to worry about finding the correct orientation during the insertion of the optical unit in the sleeve.

Further advantageous features of the present invention are listed in the dependent claims.

The present invention will now be illustrated in detail, by way of example only, with reference to the accompanying drawings, in which.

In the following description, the term proximal indicates the portion of the arthroscope that, when in use, is located in the vicinity of the patient; while the term distal is used to indicate the portion of the arthroscope that, when in use, is close to the surgeon.

In the drawing, 1 indicates the arthroscope object of the present invention. It comprises an optical unit 10 and a sleeve 20, which can be coupled to one another when in use.

The optical unit 10 comprises an elongated portion 11 having a cylindrical shape with a constant circular section, in which the axial extension, along an axis Y, has a characteristic longitudinal dimension greater than its cross-section. At a proximal end thereof, the elongated portion 11 has an optical acquisition area 11.1. Further, the optical unit 10 comprises a coupling portion 12 having a cylindrical shape with a circular cross section greater than the elongated portion 11 and integrally formed therewith, and a distal portion 13, preferably in the shape of a truncated cone, integral with the coupling portion 12, which acts as a manoeuvring portion.

On the outer surface of the optical unit 10 there are an inlet 14, which is coupled to a light source (not shown), and a pair of locking elements 16.1, 16.2 suitable to fasten the optical unit 10 to the sleeve 20.

At a free end 13a of the distal portion 13 of the optical unit 10 there is a connector 15 for the coupling of the optical unit to an optical acquisition instrument, for example a camera (not shown).

Optical transmission means (not shown), such as optical fibres for light conduction and imaging of the operative site, are present within the optical unit 10. Said optical fibres are coupled to a light source through the inlet 14 and to an optical acquisition instrument, such as a camera, via the connector 15. It should be noted that the optical acquisition area 11.1 has an optical lens.

The sleeve 20 appears as a cylindrical body with open opposite ends 21.1 and 21.2, whose central axis coincides with an axis X. The sleeve 20 has a proximal portion 21 having a cylindrical shape with a constant circular section, in which the axial extension, along an axis X, has a characteristic longitudinal dimension greater than its cross-section. The sleeve 20, integral with the proximal portion 21, has a middle portion 22 with a circular cross section greater than the proximal portion 21. The middle portion 22 ends at a distal portion 26.

The portions 21, 22 and 26 of the sleeve 20 have circular sections with different radii, preferably decreasing in the proximal direction along the axis X. It is therefore possible to identify, along the axis X, sections of the sleeve 20 with increasing radii, in the proximal—distal direction, where the proximal portion 21 has the smallest radius and the middle portion 22 has an increased radius with respect to the proximal portion 21, but smaller than the distal portion 26, which therefore has a radius greater than the other two portions 21 and 22.

The sleeve 20 has a through axial cavity 25 adapted to receive, in its interior, a substantial part of the optical unit 10. In particular, when the arthroscope 1 is in its working configuration, the elongated portion 11 of the optical unit 10 is inside the axial cavity next to the proximal portion 21; the coupling portion 12 of the optical unit 10 is next to the middle 22 and proximal 26 portions.

An abutment area 27, whose function will be explained below, is inside the middle portion 22.

On the outer wall of the middle portion 22 of the sleeve 20 there are two holes (not shown in the figure), designed to put in fluid communication the axial cavity of the sleeve 20 with the outside. Externally to said middle portion 22 of the sleeve 20 there is a cylindrical fitting 30 carrying two nozzles 32.1 and 32.2 positioned so as to overlap with the two holes on the outer wall of the middle portion 22. Said cylindrical fitting 30 can be coupled to the middle portion 22 by interference coupling, threaded coupling, or be integrally formed with the middle portion 22.

Internally, the sleeve 20, as said, has a through axial cavity 25 and is adapted to accommodate the elongated portion 11 of the optical unit 10, so that at least a proximal part 11.1 of said elongated portion 11 protrudes from the axial cavity 25 through its proximal end 21.1, and at least part of the coupling portion 12 of said optical unit 10 is housed in the area of the middle portion 22.

The coupling portion 12 has, along its outer surface, a pair of locking elements 16.1 and 16.2, each comprising a radially flexible tab 16.11, 16.21, projecting on the respective notch 16.12, 16.22, at the free end of which there is a hook 16.13, 16.23. Moreover, along each tab 16.11, 16.22 there is a respective handling button 16.14, 16.24.

The sleeve 20 has, in its axial cavity at the distal portion 26, two undercuts 26.1 and 26.2 adapted to snap into engagement with the respective hook 16.13 and 16.23 of the locking elements 16.1 and 16.2, when the arthroscope 1 is put in place. In this manner, a quick engagement and disengagement is provided between the optical unit 10 and the sleeve 20, in order to assist the surgeon during the operative phase.

Figure 1:
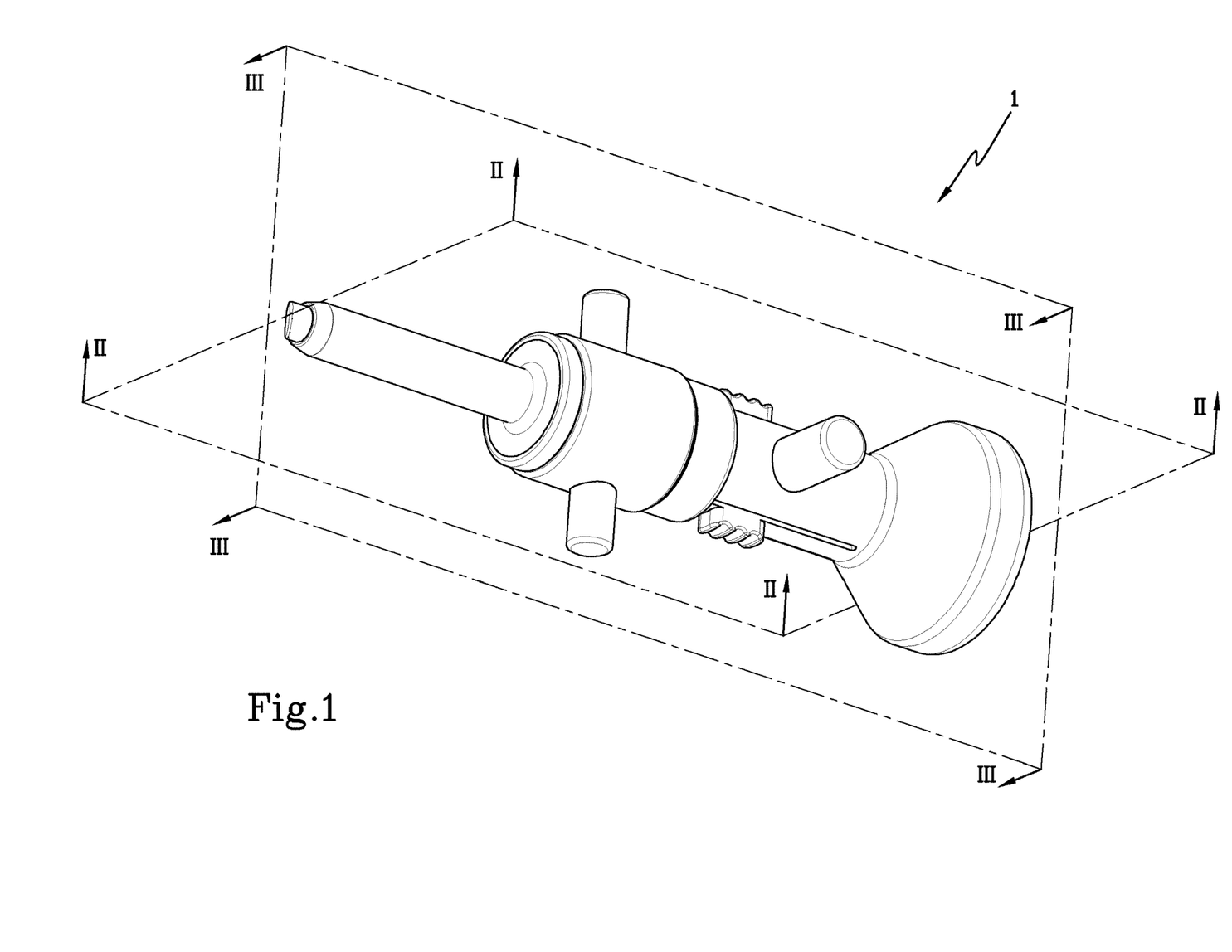
FIG. 1 is a perspective view of the arthroscope in a coupled configuration of use according to a preferred embodiment of the present invention.
Figure 2:
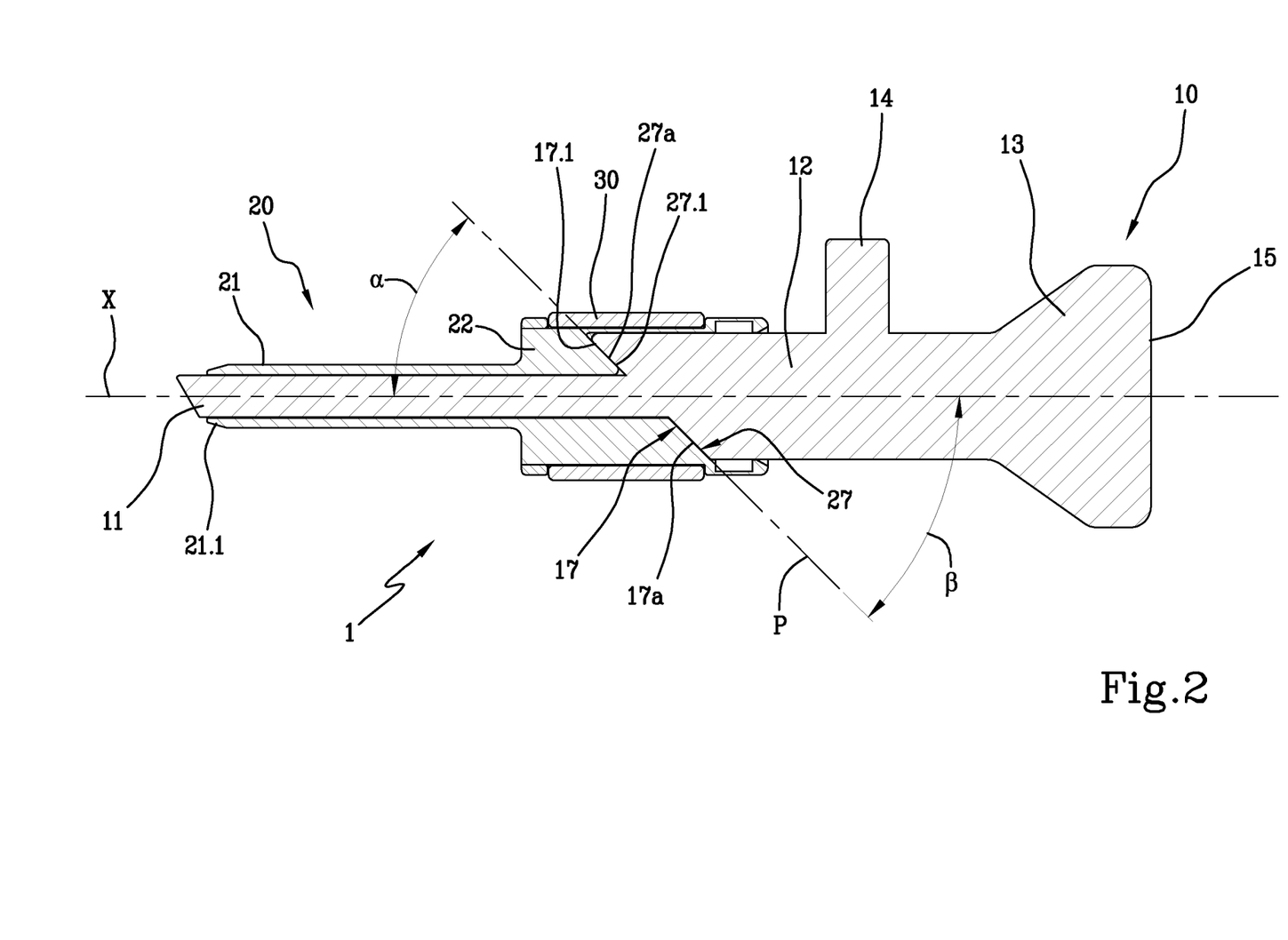
FIG. 2 is an axial section along the plane I-I of the arthroscope of FIG. 1.
Figure 3:
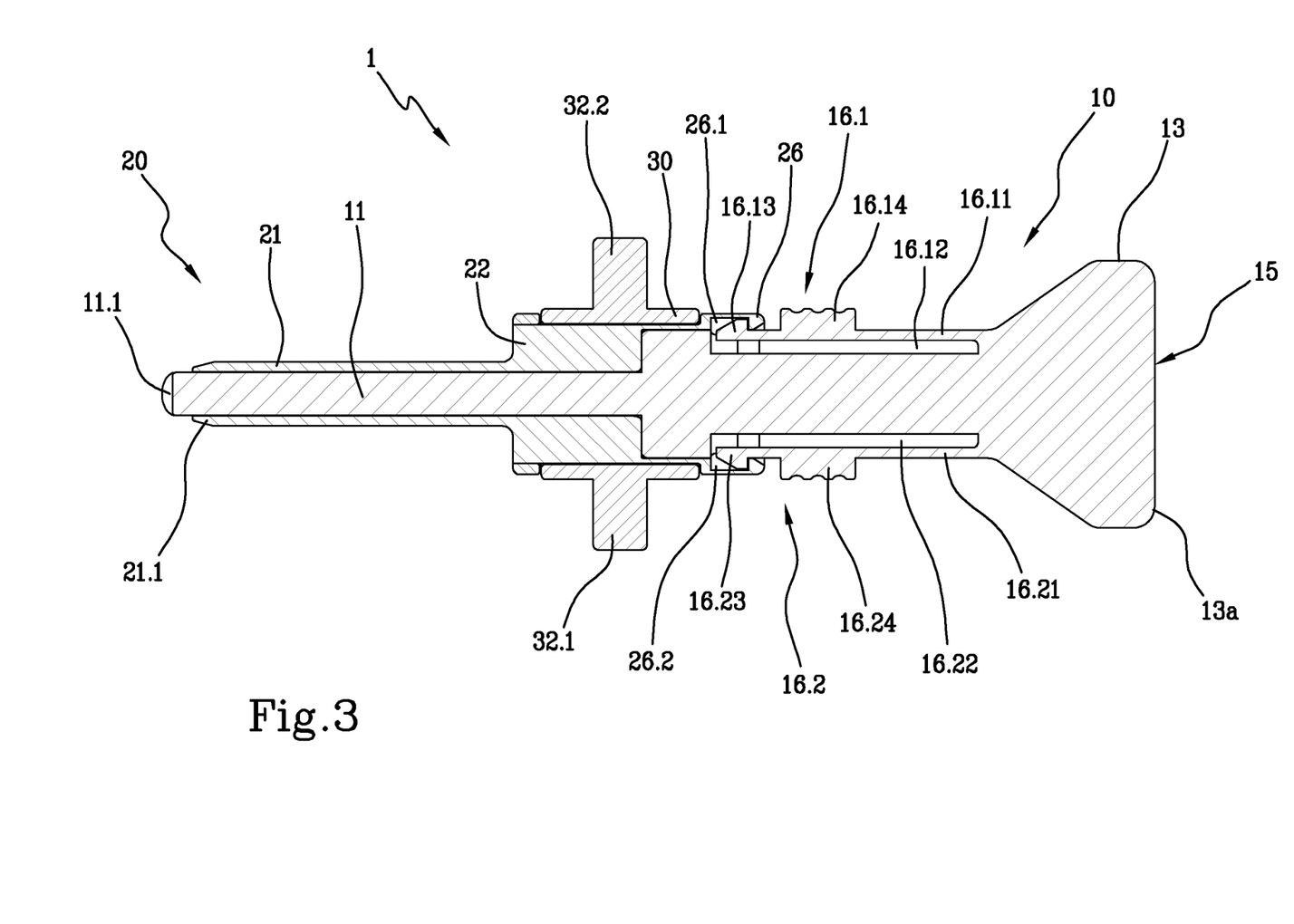
FIG. 3 is a sectional view along the plane II of the arthroscope object of the present invention.
Figure 4:
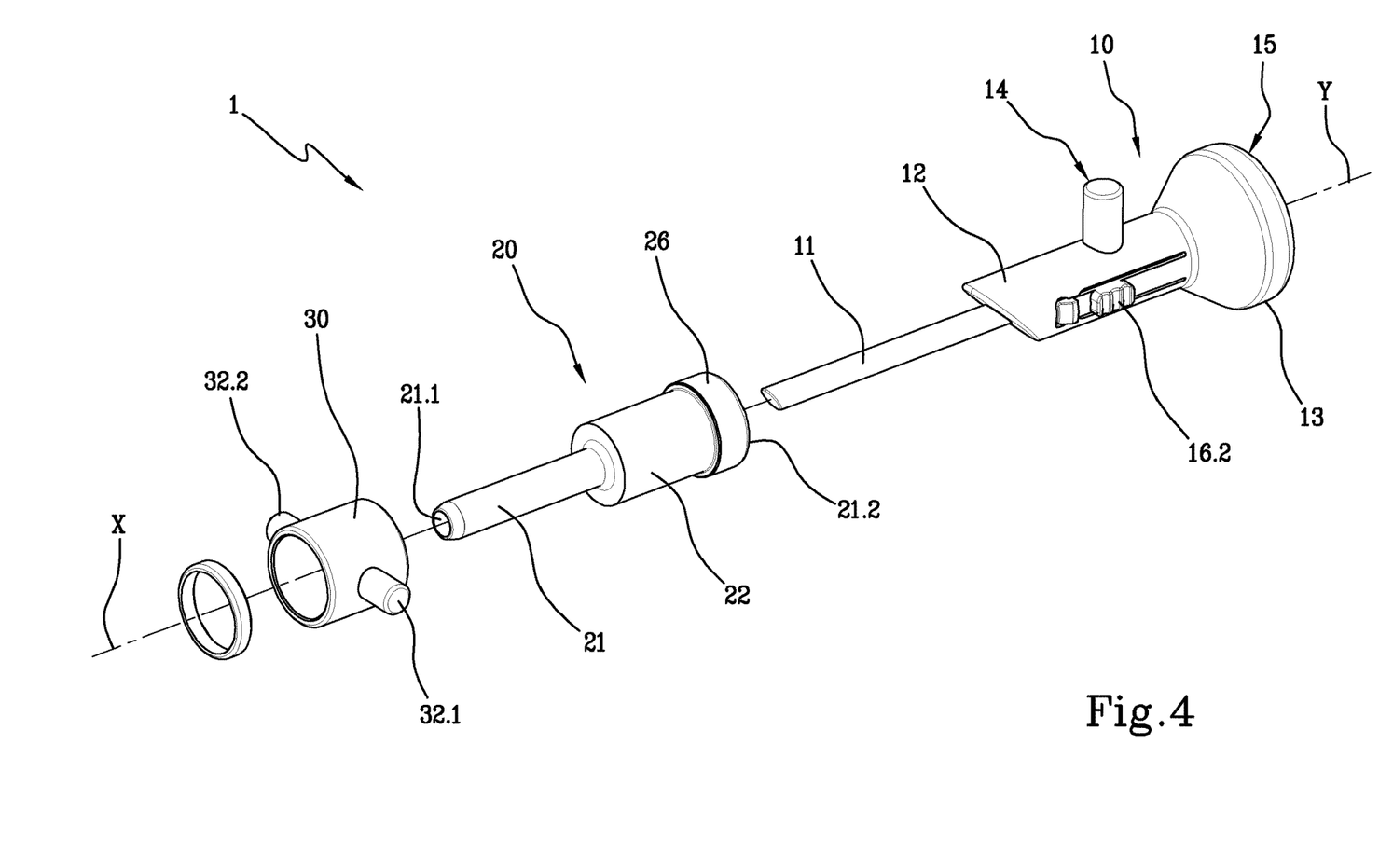
FIG. 4 is an exploded view of the arthroscope of FIG. 1.
Figure 5:
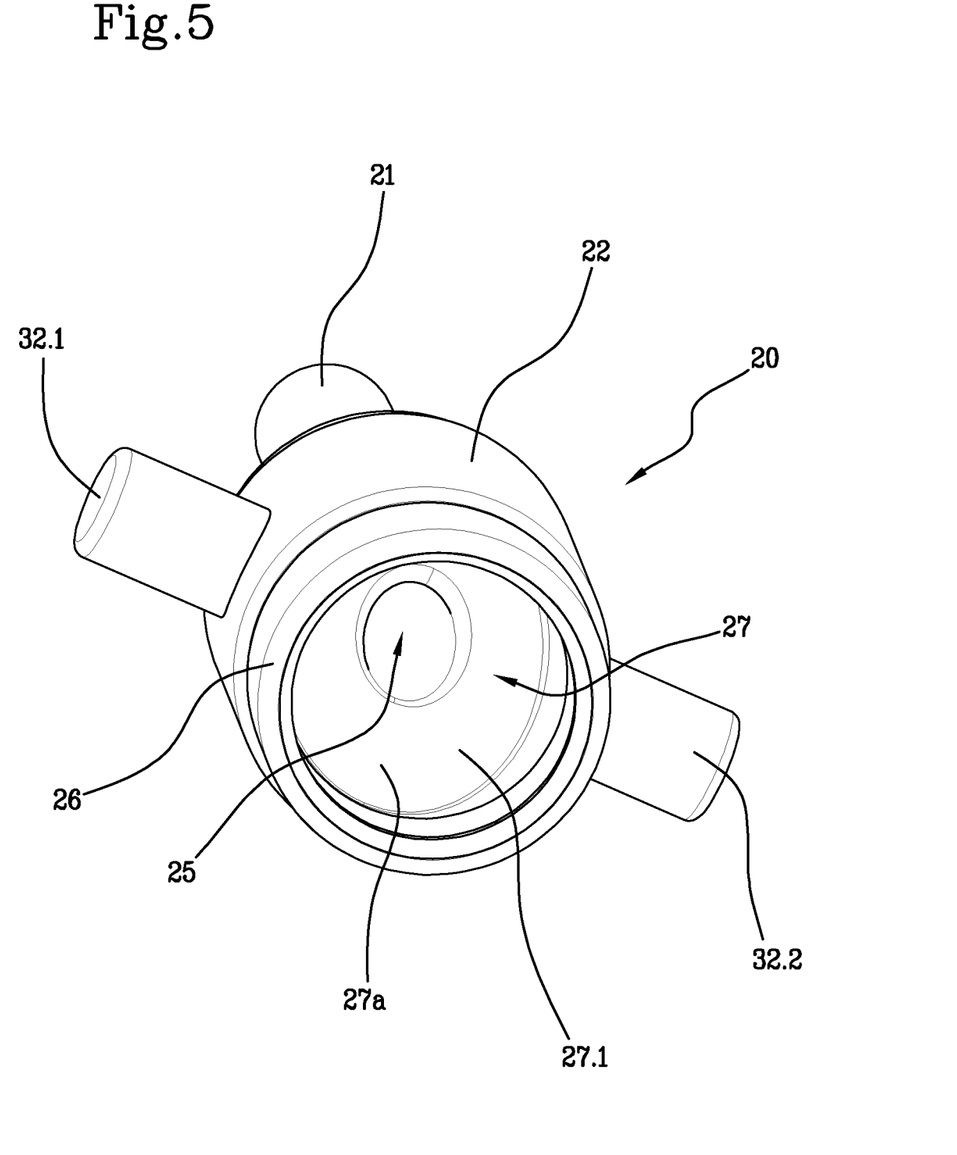
FIG. 5 is a perspective view of a first component of the arthroscope object of the present invention.
Figure 6:
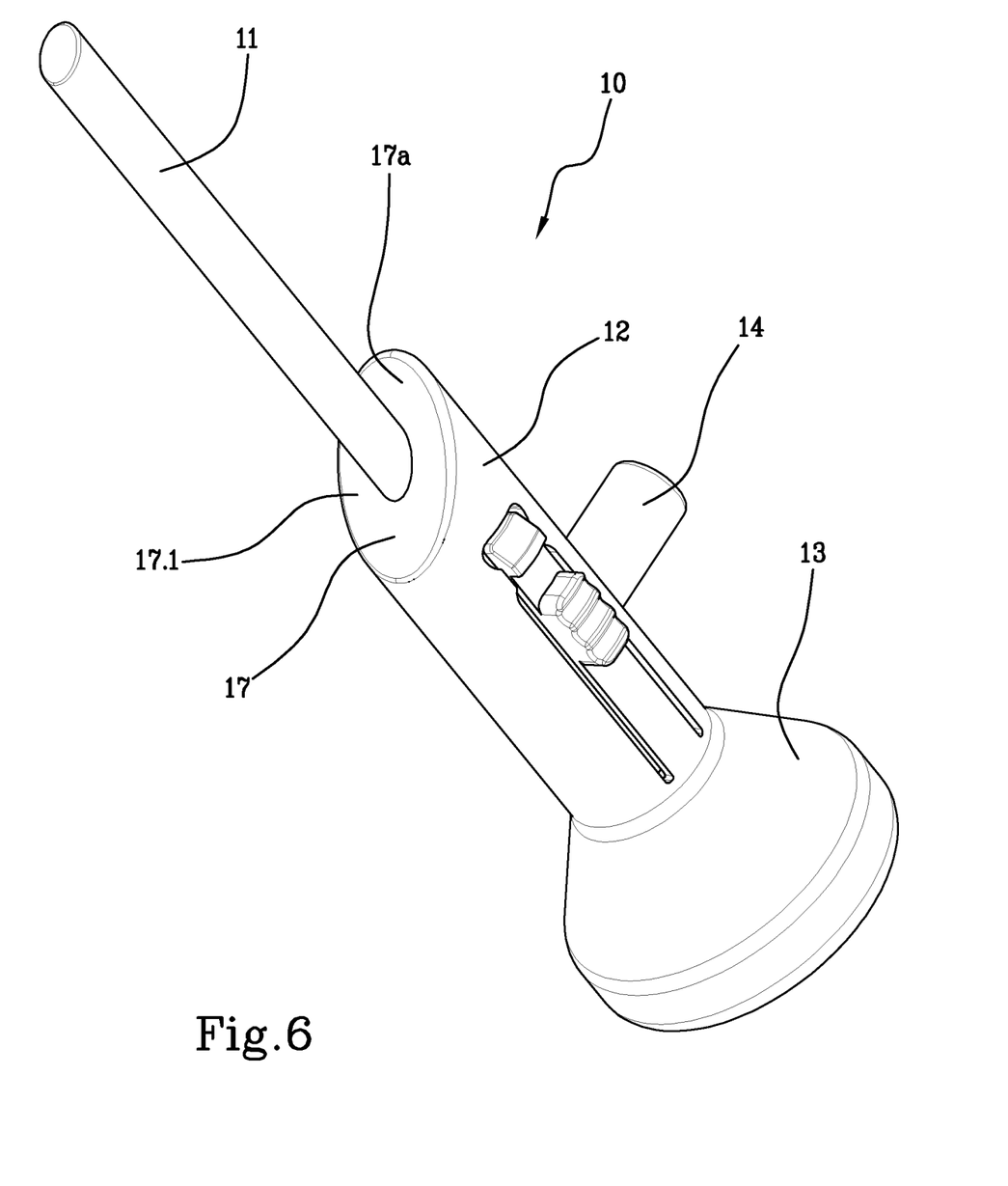
FIG. 6 is a perspective view of a second component of the arthroscope object of the present invention.

As can be seen in FIG. 2, the coupling portion 12 has a matching area 17 suitably shaped and adapted to abut against said abutment area 27 of the sleeve 20. Said abutment area 27 is formed in the axial cavity of the sleeve 20, preferably at the middle portion 22.

The matching area 17 and the abutment area 27 are shaped so as to define at least one respective pilot element 17.1, 27.1, so as to determine a univocal predefined coupling position between the sleeve 20 and the optical unit 10 when the latter is axially inserted in the sleeve 20, and to guide and automatically place the optical unit 10 in such a predefined position. Specifically, each pilot element 17.1 and 27.1 is shaped so that the univocal predefined coupling position is characterized by a predefined axial alignment along the longitudinal axis Y of the optical unit 10 (or X of the sleeve 20) with respect to the sleeve 20, and by a predefined angular orientation around said axis Y (or X) of the optical unit 10 with respect to the sleeve 20.

Preferably, the pilot element 17.1 of the matching area 17 and the pilot element 27.1 of abutment area 27 have respective inclined surfaces, referred to hereinafter as proximal surface 17a of the matching area 17 and distal surface 27a of the abutment area 27, respectively.

Positioning

After preparing the operative site, for example, after performing the necessary incisions in the limb to be operated, the surgeon proceeds by inserting, in one of the incisions, the sleeve 20 of the arthroscope 1 within said incision, after which the inner cavity of the sleeve 20 is cleaned by inserting a known shutter to clear it from any debris trapped inside. The known shutter is then extracted from the sleeve 20, while maintaining the latter in position. The optical unit 10 is then inserted in the sleeve 20 through the open distal end 21.2, by aligning the two axes X and Y of the sleeve 20 and the optical unit 10, respectively.

To do this, as a first step, the elongated portion 11 of the optical unit 10 is inserted in the axial cavity of the sleeve 20 by relative axial sliding. Said sliding movement continues until the proximal surface 17a of the matching area 17 comes into contact with the distal surface 27a of the abutment area 27. In the preferred embodiment of the present invention shown in FIG. 2, the matching area 17 has an inclined proximal surface 17a forming a pilot element 17.1 with a predefined angle α, comprised between 15° and 85°, preferably of 45°. Said pilot element 17.1 is formed by intersecting the coupling portion 12 with a plane P, which is appropriately inclined with respect to the axis Y of the optical unit 10. Similarly, the distal surface 27a of the abutment area 27 also forms a pilot element 27.1 complementary to said pilot element 17.1 of the matching area 17, which is inclined by an angle β equal to the angle α of the matching area 17, so that the two surfaces 17a and 27a are mated and fully in contact when the arthroscope 1 is in use.

Said pilot element 27.1 is formed by intersecting the middle area 22 with a plane P that is appropriately inclined with respect to the axis X of the sleeve 20. Said inclination of the inclined plane P is selected so as to provide a pilot element 27.1 which, as said, has an inclination angle β to which matches the inclination angle α of the pilot element 17.1. As shown in FIG. 2, the angles α and β are opposite each other relative to a vertex of the plane P and the axis X, so they have the same amplitude.

In this way, a univocal coupling position can be defined, as such coupling position is defined by an axial alignment between the axis X of the optical unit 10 and the axis Y of the sleeve 20, which coincide when the arthroscope is in use, and by a mutual angular position, referred to as univocal coupling orientation, between the optical unit 10 and the sleeve 20, again with respect to such axis X or Y. If the univocal coupling orientation is not complied with, the conformation of the pilot elements 17.1 and 27.1 of the matching area 17 and the abutment area 27, respectively, are such as to impose corrective rotations on the optical unit 10, to guide and position the optical unit 10 in the correct predetermined coupling position in an automatic manner. The correct coupling is considered to be reached when the matching area 17 and the abutment area 27, by sliding relative to one another in the axial direction, come into full contact. Moreover, said correct coupling causes the hooks 16.13 and 16.23 to interfere with the respective undercuts 26.1 and 26.2 of the distal area 26 of the sleeve 20, thereby producing a characteristic sound that alerts the surgeon of the correct positioning of the optical unit 10 with respect to the sleeve 20. In this configuration, the arthroscope 1 is ready to be correctly used.

It is clear to the person skilled in the art that the shape of the matching area 17 and of the abutment area 27 may vary with respect to what is described without departing from the scope of protection of the present patent. What matters is that said areas 17 and 27, by coupling to each other, assume a univocal position in the axial and rotational directions.

An alternative embodiment of the present invention, not shown, provides a matching area with a polygonal section and an abutment area shaped with a complementary cavity. In this alternative embodiment, the walls of the abutment area and the walls of the matching area act as a pilot element, the dimensions, and possibly the characteristic shapes of which determining the correct coupling orientation between the sleeve 20 and the optical unit 10.

For example, a preferred polygonal shape may be that of a pyramid, so that the matching area 17 projects proximally along the axis Y and has a pyramidal or frusto-pyramidal shape, so that it can couple and engage with the corresponding complementarily-shaped abutment area 27 having a pyramidal or frusto-pyramidal recess.

Furthermore, the matching area 17 may have, for example, a helical shape, for example a screw shape, while the abutment area 27 may assume a corresponding helical shape, for example a nut screw shape. In this hypothesized embodiment, the flanks of the screw and the nut screw act as pilot elements to guide the correct orientation of the coupling.

It will also be possible to create insertion guides consisting of lateral protrusions projecting radially from the axial cavity of the sleeve 20 suitable to engage with corresponding notches on the outer surface of the coupling portion 12 of the optical unit 10.

The invention allows many advantages and the achievement of the intended goals.

In fact, the present invention provides an arthroscope that can be put in place by the surgeon so as to automatically obtain the correct orientation of the visual field required for acting on the operative site.

In fact, the arthroscope thus provided allows any axial rotation of the optical unit with respect to the sleeve in which it is inserted to be prevented, thus maintaining the visual field of the surgeon angularly fixed and allowing for obtaining an image of the operative site that is correctly oriented in space.

The arthroscope object of the present invention avoids any misalignment and any deviation of the pointing of the optical unit, allowing the surgeon to pinpoint the desired point within the operative site. Moreover, the present invention allows the arthroscope to be positioned right away in the correct and predetermined position, avoiding subsequent troublesome and problematic repositioning attempts by the surgeon throughout the operative step.

The shape of the matching area, and consequently of the abutment area prevents relative rotation between the optical unit and the sleeve around the central axis of the two bodies, also avoiding possible micro-movements between the two portions due to machining tolerances which generate vibrations in the visual field of the surgeon.

The invention claimed is:

1. An arthroscope comprising:
   a sleeve having an internally hollow proximal portion configured to be at least partially positioned in contact with a body of a patient, and an internally hollow middle portion connected to said proximal portion so as to create a through axial cavity, the internally hollow middle portion having an abutment area; and
   an optical unit having an elongated portion and a coupling portion, both portions being configured to be at least partially received inside the through axial cavity of the sleeve, said coupling portion having a matching area configured to be coupled with said abutment area,
   wherein said matching area and said abutment area are shaped so as to each have at least one pilot element, each pilot element defining an inclined surface, said inclined surface of the pilot element of the matching area being inclined with respect to a longitudinal axis of the optical unit and the sleeve according to a first angle, and said inclined surface of the pilot element of the abutment area being inclined with respect to the longitudinal axis according to a second angle, the first and second angles being opposite each other relative to a vertex and having the same amplitude, such as, when the two inclined surfaces are coupled together, to determine a univocal predefined coupling position between the sleeve and the optical unit, said univocal predefined coupling position providing axial alignment along said longitudinal axis with respect to the sleeve and a predefined angular orientation, around said axis, with respect to the sleeve, for guiding and automatically positioning the optical unit in said univocal predefined coupling position inside the sleeve.

2. The arthroscope according to claim 1, wherein the first angle and the second angle are comprised between 15° and 85°.

3. The arthroscope according to claim 2, wherein the first angle and the second angle are 45°.

4. The arthroscope according to claim 1, wherein said inclined surfaces are obtained by cutting the middle portion of the sleeve and the coupling portion of the optical unit along respective a plane inclined with respect to said axis.

5. The arthroscope according to claim 1 wherein the at least one pilot element of the abutment area comprises a first pilot element and the at least one pilot element of the matching area comprises a second pilot element, wherein the first pilot element is complementarily shaped with respect to said second pilot element so as to define the predefined coupling position.

6. An arthroscope according to claim 1, wherein the coupling portion of the optical unit comprises one or more locking elements for fastening the optical unit to the sleeve.

7. The arthroscope according to claim 6 wherein the one or more locking elements comprise two locking elements, each locking element being configured to couple with a respective undercut formed in a distal portion of said sleeve.

8. The arthroscope according to claim 7, wherein said locking elements comprise radially flexible fast-coupling tabs.

\* \* \* \* \*